United States Patent
Barbaro et al.

(10) Patent No.: US 7,535,232 B2
(45) Date of Patent: May 19, 2009

(54) FIELD-EFFECT DEVICE FOR THE DETECTION OF SMALL QUANTITIES OF ELECTRIC CHARGE, SUCH AS THOSE GENERATED IN BIO-MOLECULAR PROCESS, BOUND IN THE VICINITY OF THE SURFACE

(75) Inventors: Massimo Barbaro, Cagliari (IT); Annalisa Bonfiglio, Cagliari (IT); Luigi Raffo, Cagliari (IT)

(73) Assignee: Consiglio Nazionale Delle Ricerche, Genova (IT)

( * ) Notice: Subject to any disclaimer, the term of this patent is extended or adjusted under 35 U.S.C. 154(b) by 0 days.

(21) Appl. No.: 11/570,255

(22) PCT Filed: Jun. 9, 2005

(86) PCT No.: PCT/EP2005/052655

§ 371 (c)(1),
(2), (4) Date: Dec. 8, 2006

(87) PCT Pub. No.: WO2005/121765

PCT Pub. Date: Dec. 22, 2005

(65) Prior Publication Data

US 2007/0247170 A1    Oct. 25, 2007

(30) Foreign Application Priority Data

Jun. 9, 2004    (IT)    ............ TO2004A0386

(51) Int. Cl.
*G01N 27/60*    (2006.01)

(52) U.S. Cl. .............. 324/453; 324/658; 324/109
(58) Field of Classification Search .............. None
See application file for complete search history.

(56) References Cited

U.S. PATENT DOCUMENTS 5,414,284 A *    5/1995    Baxter et al. ............ 257/253

(Continued)

FOREIGN PATENT DOCUMENTS

DE    42 39 319 A1    4/1993
WO    WO 03/056322 A1    7/2003

OTHER PUBLICATIONS 57.5: Low Drift Air-Gap CMOS-FET Gas Sensor: IEEE, 2002; Pawel, et al.

(Continued)

*Primary Examiner*—Timothy J. Dole
*Assistant Examiner*—Thomas F. Valone
(74) *Attorney, Agent, or Firm*—Sughrue Mion, PLLC

(57) ABSTRACT

The device (1) allows the detection of small quantities of electrical charge (Qs) utilised for recognition of the gybridisation process of a single strand of DNA. It comprises a chip (2) in which is integrated an MOS device having a floating gate (7) a first portion (7a) of which extends in facing relation to a recess (8) formed in a surface of the chip (2) and accessible from outside the chip (2) and operable to retain an electrical charge (Qs) to be measured bound to it. A second portion (7b) of the gate (7) of the MOS device is coupled to a control electrode, (10) of the chip (2) by means of a capacitor (12) of predetermined value within the chip (2).

6 Claims, 4 Drawing Sheets

U.S. PATENT DOCUMENTS

| | | | | |
|---|---|---|---|---|
| 6,657,269 | B2* | 12/2003 | Migliorato et al. | 257/414 |
| 6,974,716 | B2* | 12/2005 | Hsiung et al. | 438/49 |
| 7,019,343 | B2* | 3/2006 | Chou et al. | 257/253 |
| 7,049,645 | B2* | 5/2006 | Sawada et al. | 257/292 |
| 7,321,143 | B2* | 1/2008 | Kunath et al. | 257/288 |
| 2003/0152929 | A1 | 8/2003 | Howard | |
| 2004/0207384 | A1* | 10/2004 | Brederlow et al. | 324/71.5 |

OTHER PUBLICATIONS

"Hybrid-gate suspended field-effect transistors for gas-sensing"; Zimmer.

Burgmair, M. et al., "Field effect transducers for work function gas measurements: device improvements and comparison of performance", Sensors And Actuators B, 2003, pp. 183-188, vol. 95.

* cited by examiner

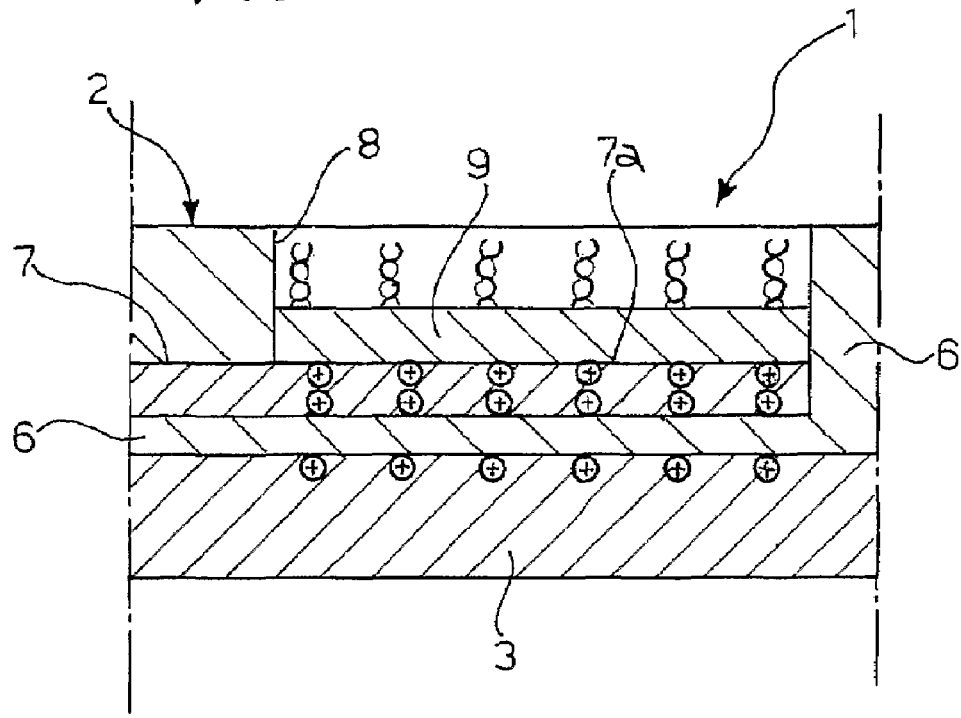
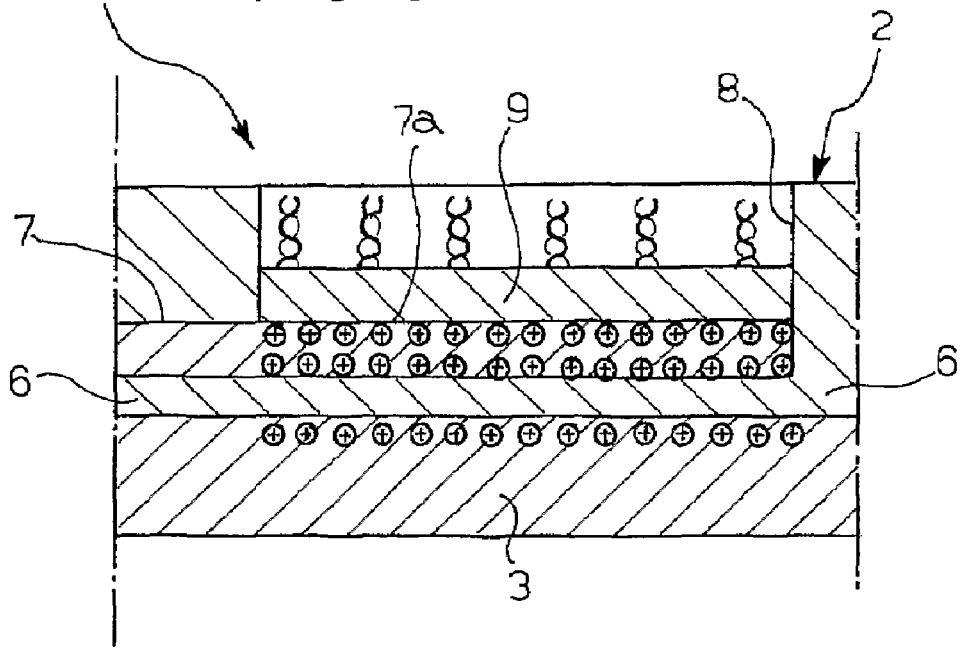

FIELD-EFFECT DEVICE FOR THE DETECTION OF SMALL QUANTITIES OF ELECTRIC CHARGE, SUCH AS THOSE GENERATED IN BIO-MOLECULAR PROCESS, BOUND IN THE VICINITY OF THE SURFACE

BACKGROUND OF THE INVENTION

The present invention relates to a field-effect device for the detection of small quantities of electric charge, such as those generated in bio-molecular processes, bound in the vicinity of its surface.

In the scientific literature there are known devices which exploit the measurement of the electric charge for particular applications by means of the use of a single device such as an ISFET. ISFET represents an evolution of the MOS transistor and allows the measurement of the pH of a solution by measuring the electric charge carried by the ions dissolved in the solution, bound to particular "binding sites" on the surface of the silicon. Devices for detecting small quantities of electric charge are utilised for recognition of the hybridisation process of a single strand of DNA. For this purpose the most widely used technique at the moment, however, involves the use of a micro-array of optically read fluorescent markers; single strand portions of DNA are fixed to a substrate of silicon dioxide (glass), and the complementary strand which can be expected to be found in an analysis sample is labelled with fluorescent molecules (markers); the hybridisation phase then proceeds in which the re-combination of the complete double helix is encouraged if the gene or the portion of DNA sought is located in the analysis sample. If the sample contains the gene sought, this strand binds itself to that fixed on the surface of the glass, thereby "gluing" the fluorescent marker onto a particular portion of the substrate, and the occurrence of hybridisation (and therefore the presence of the gene) can then be verified by means of an optical analysis of the surface. This method involves the use of costly equipment (above all optical systems) which is large and not transportable.

In recent years scientific research has made considerable efforts to achieve direct detection of the DNA hybridisation process by means of a measurement of electronic type. Plasma techniques have now been proposed, and techniques based on the use of the MEMS structures (Micro-Electrical-Mechanical-Systems) which, for example, make use of the so-called cantilevers and micro-balances. Other methods are based on the use of micro-electrodes, or on capacitive effects, others still utilise field effect transistors (FET).

International patent application WO-03/073088 describes a FET sensor device having a single floating gate.

U.S. patent application US-2003/152929 describes an elaborate system for detecting the hybridisation of individual portions of a DNA strand by means of charge measurements which are effected by reference to a cell containing known recombinant DNA (double helix).

International patent application WO-03/014722 describes the use of a field effect transistor for the detection of hybridisation of single strands of DNA.

One object of the present invention is to provide an improved device for the detection of very small quantities of electrical charge, which can be formed in a relatively simple and economic matter and which allows a direct reading of a charge variation without the necessity for external apparatus.

This and other objects are achieved according to the invention with a device comprising a chip in which is integrated in a MOS device having a floating gate, a first portion of which extends in facing relation to a recess formed in a surface of the chip and is covered by an interface layer which is accessible from outside the chip and is able to retain an electrical charge to be measured, applied to it; a second portion of the gate of the said MOS device being coupled to a control electrode of the chip by means of a capacitor of predetermined value within the chip.

Conveniently, the chip of the device for detecting small quantities of electrical charge according to the invention can be formed with a standard CMOS process. This allows production at low cost and the possibility of being able to exploit continuous improvements of CMOS technology in a direct and immediate manner, in particular in terms of scale of integration and availability of processor modules and CAD products for design purposes which have been already developed.

Further characteristics and advantages of the invention will become apparent from the following detailed description, given purely by way of non-limitative example, with reference to the attached drawings, in which:

BRIEF DESCRIPTION OF THE DRAWINGS

FIGS. 4 and 5 are similar views to those of FIG. 2 and refer to two different operating conditions of a device according to the invention;

DETAILED DESCRIPTION OF THE INVENTION

Figure 1:
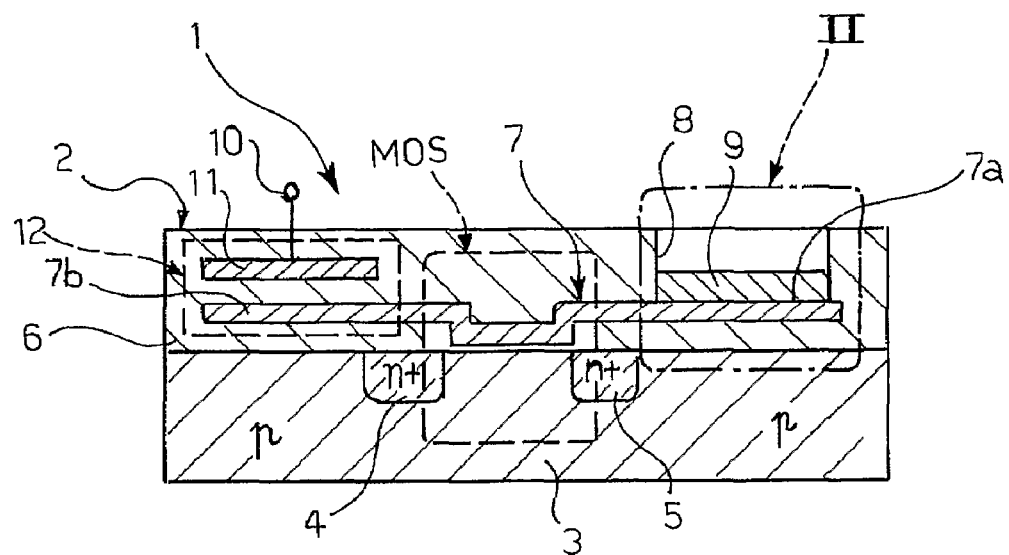
FIG. 1 is a schematic qualitative representation, in transverse section, of a device according to the present invention.

In FIG. 1, a device according to the invention for the detection of small quantities of electrical charge is generally indicated 1. This device essentially comprises a chip 2 integrally formed with a standard CMOS process.

The chip 2 comprises a substrate 3 of silicon, with p-type doping for example. In this substrate, with techniques known per se, are formed to zones 4 and 5 with n+ type doping. A layer 6 of silicon dioxide (SiO2) is formed on the substrate 3 with techniques known per se. In the chip 2 there is formed a floating gate 7, for example of polysilicon, which is separated from the substrate 3 by a layer of silicon dioxide.

The intermediate portion of the floating gate 7, joined to the zones or regions 4 and 5, co-operates in forming an MOS device, ideally enclosed within the broken line in FIG. 1.

The floating gate 7 has a first portion 7a which extends in facing relation with respect to a recess 8 formed in the upper surface of the chip 2. This recess created in the passivation layer of the chip extends as far as the surface of the gate 7 possibly passing through the connections with metal layers (on which only is it possible to open windows into the passivation in current standard CMOS processes) and within this recess the surface of the portion 7a of the gate 7 is accessible from outside the chip 2 (also indirectly through the connection with metalisations). On this surface it is possible to create a possible interface layer 9 able to bind the electrically charged material and to retain a small quantity of electrical charge to be measured, which is applied to it in use.

The gate 7 has a further portion 7b coupled to a control electrode 10 of the chip 2 by means of a capacitor of predetermined value within the chip 2 itself.

For this purpose, as is shown in FIG. 1, within the chip 2, and with techniques known per se, there can be formed, in facing relation and spaced from the portion 7b of the gate 7, a layer 11 of conductive material, for example of polysilicon (a material which, incidentally, can be also utilised for the formation of the gate 7) accessible from the outside with techniques known per se.

The layer 11 and the portion 7b of the gate 7, with the layer of dielectric material (silicon dioxide) interposed between them, form a capacitor generally indicated 12. The control electrode 10 is therefore capacitively coupled to the gate 7 and serves in use to fix the working point of the device and as a reference electrode.

Figure 3:
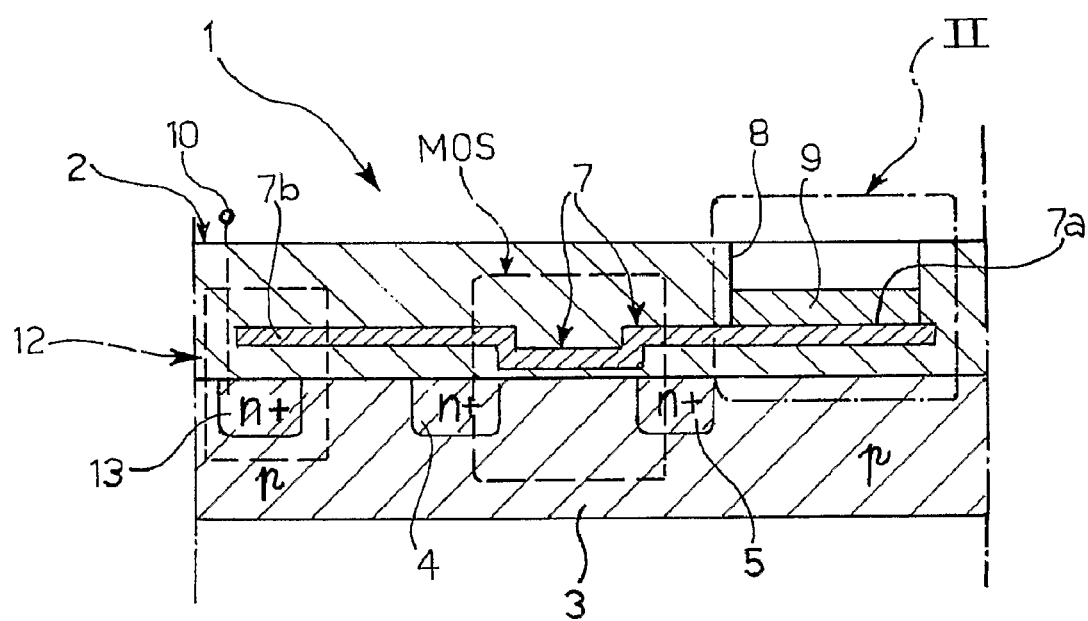
FIG. 3 is similar to FIG. 1 and shows a variant embodiment.

Alternatively, as is shown in FIG. 3, in facing relation to the portion 7b of the gate 7 in the substrate 3 there is formed by diffusion a further zone 13 of n+ type doping, functioning as a control gate. This zone 13 can be rendered accessible from the outside of the device 1 in a manner known per se.

In general, devices according to the invention which have been described above with reference to FIGS. 1 and 3 can be considered as MOS devices with an accessible floating gate which becomes the part sensitive to charge bound in a recess created on it, with a supplementary control electrode capacitively coupled to the floating gate. These devices have been called CFET (Charge-Induced Field Effect Transistor) by the inventors and work in the following manner.

Figure 2:
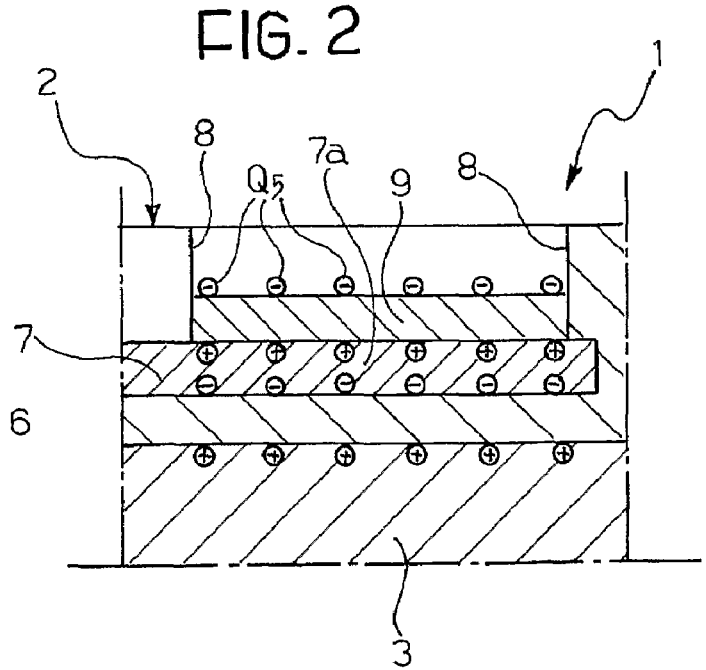
FIG. 2 shows, on an enlarged scale, a portion indicated II in FIG. 1.

With reference to FIG. 2, in use a quantity Qs of (negative) electrical charge is trapped in the recess 8 via the interface layer 9. Correspondingly, in the portion 7a of the floating gate 7 a separation of corresponding positive and negative charges is induced, which lodge at the interface between the gate and the layer 9 and, respectively, at the interface between the gate and the silicon dioxide layer 6.

Corresponding positive charges are induced in the substrate 3 at the interface between this substrate and the silicon dioxide layer 6. This then creates a potential difference between the floating gate 7 and the silicon substrate 3.

The charge Qs trapped at the interface layer 9 causes a variation in the threshold voltage of the device, with an effect which is approximately quantified by the following expression:

$$V_{THF} \approx V_{TH} - \frac{Q_{F0} + Q_S}{C_{CF} + C_{FB}}$$

where $V_{THF}$ is the resultant threshold voltage by the effect of the bound charge Qs, $V_{TF}$ is the starting threshold voltage or rather the voltage in the absence of the charge Qs, $C_{CF}$ is the capacity of the capacitor 12, $C_{FB}$ is the capacity between the floating gate 7 and the substrate 3, and $Q_{FO}$ is the charge trapped in the floating gate 7.

In the above-indicated expression all the quantities have fixed values except Qs and $V_{THF}$, and the threshold voltage of the device can therefore be utilised to evaluate the bound charge Qs.

The device according to the invention is therefore able to recognise bio-molecular processes characterised by a charge variation.

In FIGS. 4 and 5 is schematically and qualitatively illustrated the application of the device according to the invention to the recognition of hybridisation of DNA.

Each oligonucleotide which constitutes a sequence of DNA is characterised by a negative charge. A single helix sequence is therefore characterised by the presence of a negative charge equal to half that possessed by a double helix sequence of the same length.

In FIG. 4 is shown the detail II of the device according to FIG. 1 or 3, in the condition in which on the interface layer 9 is fixed a negative electrical charge of the single helix sequence.

With reference to FIG. 5, when hybridisation of this sequence has taken place a charge which is bound to the interface layer 9 of the device is doubled. The potential difference between the floating gate 7 and the substrate 3 is correspondingly increased.

Figure 6:
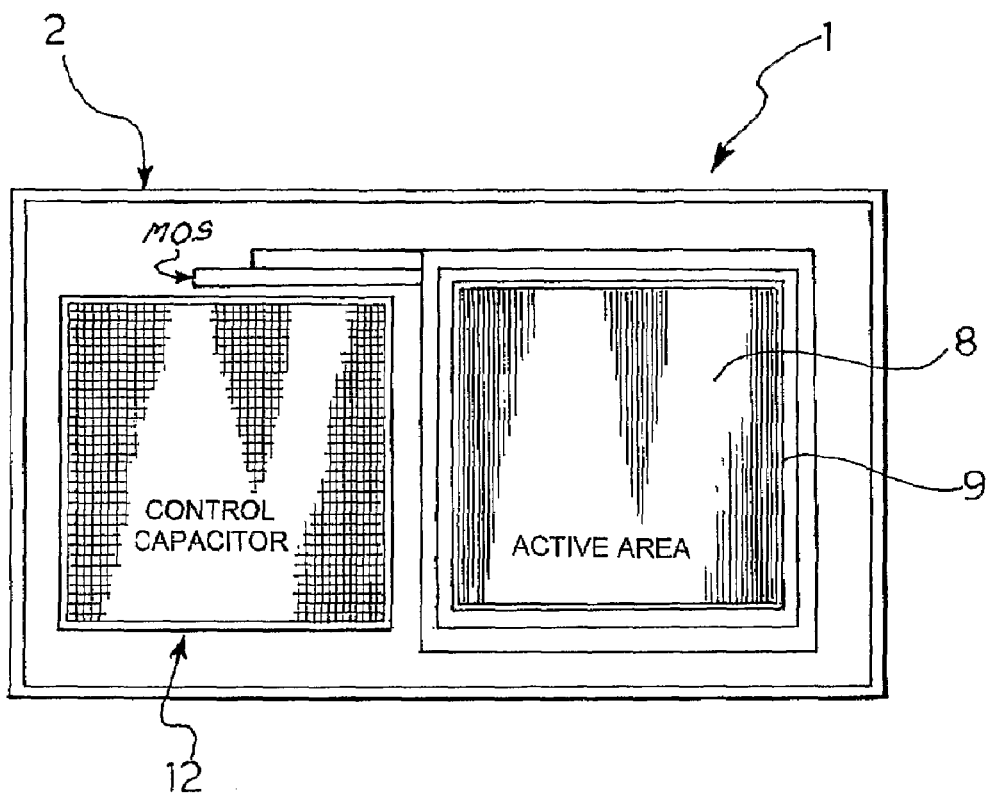
FIG. 6 is a schematic plan view of a possible layout of the device according to the invention.

In FIG. 6 there is shown purely by way of example a possible layout of the device 1 according to FIG. 1. In this layout parts and elements which have already been described are indicated with the same reference numerals utilised before.

Figure 7:
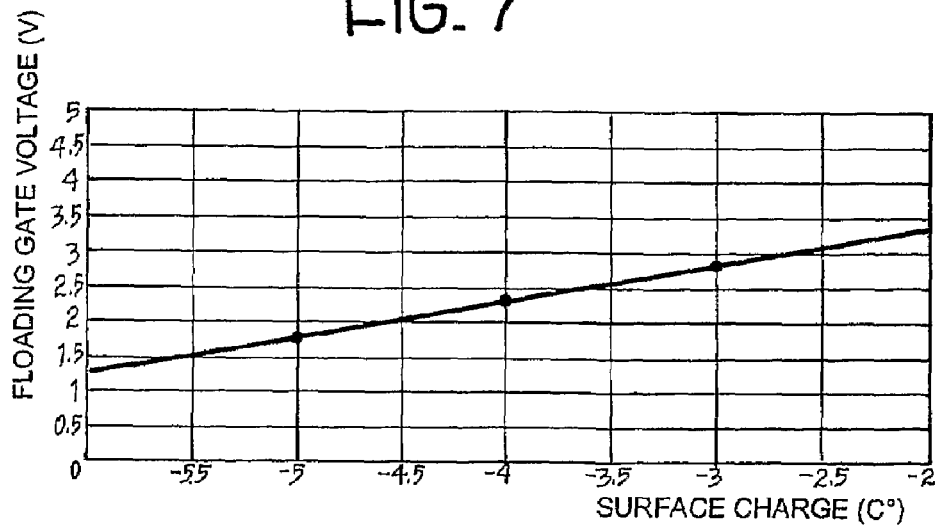
FIG. 7 is a diagram which shows the characteristic of a device according to the invention, or rather the variation of the voltage on the floating gate, plotted along the ordinate, as a function of the charge bound to the sensor, plotted on the abscissa.

In FIG. 7 there is shown a graph which illustrates the essentially linear dependence of the voltage on the floating gate 7 to variations of charge density bound in a device according to the invention. This graph refers in particular to a device according to the invention with an active area (or rather the area of the interface layer 9) of 100 μm×100 μm formed with an 0.8 μm CMOS process (AMS CYX).

Naturally, the principle of the invention remains the same the embodiments and details of construction can be widely varied with respect to what has been described illustrated purely by way of non-limitative example without by this departing from the ambit of the invention as defined in the annexed claims.

The invention claimed is:

1. A device (1) for detecting small quantities of electrical charge (Qs) comprising:
    a chip (2) in which is integrated a MOS device having a floating gate (7) a first portion (7a) of which extends in facing relation with a recess (8) formed in the surface of the chip (2) and accessible from outside the chip (2) and able to retain an electrical charge (Qs) to be measured bound to it; a second portion (7b) of the gate (7) of the said device MOS being coupled to a control electrode (10) of the chip (2) by means of a capacitor (12) of predetermined value within the chip (2).

2. A device according to claim 1, wherein said chip (2) is formed with a standard CMOS process.

3. A device according to claim 1, wherein said first portion (7a) of the floating gate (7) is at least partially covered by a layer of interface material (9) which can bind an electrically charged material applied to it.

4. A device according to claim 1, wherein said second portion (7b) of the floating gate (7) is capacitively coupled to an overlying supplementary layer (11) of conductive material, connected to a control electrode (10) accessible from outside the device (1).

5. A device according to claim 1, wherein said MOS device comprises a substrate (3) of semiconductor material with p-type doping, and wherein said second portion (7b) of the floating gate (7) is capacitively coupled to a zone (13) of this substrate (3) which has an n+ type doping and which is connected to a control electrode (10) accessible from outside the device (1).

6. A device according to claim 4, wherein the supplementary layer is polysilicon.

* * * * *